(12) United States Patent
Harrel

(10) Patent No.: US 7,798,813 B1
(45) Date of Patent: Sep. 21, 2010

(54) ROTARY TISSUE REMOVING INSTRUMENT

(76) Inventor: Stephen K. Harrel, 4510 Ridge Rd., Dallas, TX (US) 75229

( * ) Notice: Subject to any disclaimer, the term of this patent is extended or adjusted under 35 U.S.C. 154(b) by 125 days.

(21) Appl. No.: 11/986,150

(22) Filed: Nov. 20, 2007

(51) Int. Cl.
*A61C 5/00* (2006.01)
(52) U.S. Cl. .................. 433/215; 433/118; 433/165
(58) Field of Classification Search ......... 433/141–144, 433/118, 165, 215; 606/79–85, 179, 180; 600/562–568, 570; 33/30, 408, 639
See application file for complete search history.

(56) References Cited

U.S. PATENT DOCUMENTS

| 3,683,891 | A | * | 8/1972 | Eskridge et al. ............. 600/564 |
| 5,275,609 | A | | 1/1994 | Pingleton et al. |
| 5,290,303 | A | | 3/1994 | Pintleton et al. |
| 5,762,069 | A | * | 6/1998 | Kelleher et al. ............. 600/564 |
| 6,764,452 | B1 | * | 7/2004 | Gillespie et al. ............. 600/567 |
| 7,611,473 | B2 | * | 11/2009 | Boock et al. ................. 600/564 |
| 2002/0138020 | A1 | * | 9/2002 | Pflueger ..................... 600/562 |
| 2007/0198019 | A1 | * | 8/2007 | Schomer et al. ............... 606/79 |

OTHER PUBLICATIONS

Sullivanschein Product Catalog, date unknown, pp. 224-225.

* cited by examiner

*Primary Examiner*—Cris L Rodriguez
*Assistant Examiner*—Eric Rosen
(74) *Attorney, Agent, or Firm*—Roger N. Chauza, P.C.

(57) ABSTRACT

A rotatable tissue removing instrument having a tissue engaging member. The tissue engaging member includes one or more prongs or barbs, or both, which grab the strands of granulation tissue and cause the tissue to be wrapped around the tissue engaging member. The granulation tissue continues to be wrapped around the tissue engaging member until pulled free from both the tooth and the bone.

10 Claims, 3 Drawing Sheets

ROTARY TISSUE REMOVING INSTRUMENT

BACKGROUND OF THE INVENTION

Medical and dental practice often requires the surgical removal of both hard and soft tissue in the treatment of a patient. The removal of damaged tissue or scar tissue is often necessary in order to prevent deterioration of associated or neighboring healthy tissue. For example, in the treatment of periodontal diseases, such as periodontitis, the removal of granulation tissue is necessary in order to arrest further deterioration of both the hard bony tissue and soft gingival tissue. Granulation tissue is the diseased gingival tissue that is attached to the bone around the tooth. The granulation tissue has a stringy consistency and must be removed before the healthy gingival tissue and the bone can regenerate and reattach to the tooth.

The current practice in removing the granulation or scar tissue adjacent a tooth is with the use of a curette. By continually scraping the granulation tissue with the curette, the sinewy tissue fibers are disconnected from the damaged bone and removed. Generally the tissue is scraped by a curette and then suctioned by other equipment to remove the tissue fragments. In some instances, the suction instrument and curette scraping operation is conducted simultaneously.

The removal of granulation tissue by a curette is a time consuming and tedious process, often taking 5-8 minutes per tooth. Depending upon the number of teeth which are afflicted, it can be appreciated that the entire process can be stressful, both for the patient as well as the surgeon.

A tissue grinding bur well adapted for removing granulation tissue is disclosed in U.S. Pat. No. 5,122,153 by Harrel. A bur rotates within a tubular member to which suction is applied. The bur has sharp cutting edges. As the bur rotates within the suction tube, it pulls the sinewy granulation tissue therein and grinds the tissue strands into small particles. The annular edge of the opening in the suction tube is sharpened to facilitate the removal of the granulation tissue from the healthy tissue, as well as from the bone surface.

In both the medical and dental areas of practice, the tissue to be removed is often in a small or very inaccessible location. This is especially true in periodontal operations where the granulation tissue is recessed far below the gingival line, in areas of bone deterioration near the root of the tooth. In this instance it becomes extremely difficult to cut or scrape the granulation tissue and remove it.

From the foregoing, it can be seen that a need exists for an instrument which can remove tissue in a more expedient manner that heretofore known. A further need exists for a tissue removing instrument which is effective to remove tissue in narrow or tight places. Yet another need exists for a tissue removing instrument which wraps the sinewy tissue around a shank so that it can be accumulated thereon and pulled free from the hard bone surface.

SUMMARY OF THE INVENTION

In accordance with the principles and concepts of the invention, there is disclosed a tissue removing instrument that is rotatable with a hand-held tool. The tissue removing instrument includes a tissue engaging member having protrusions, including prongs, or barbs, or both, for grabbing tissue so that the tissue is wrapped around the instrument and pulled free from the body of tissue.

In accordance with one embodiment of the invention, disclosed is a tissue removing instrument that includes a shank adapted for attachment to a tool for rotation of said shank. The shank has formed at the end thereof a tissue engaging member. The tissue engaging member has one or more protrusions for engaging tissue and causing the tissue to be wrapped around the tissue engaging member.

In accordance with a feature of the invention, the tissue is pulled free from the body of tissue without cutting the tissue.

In accordance with another embodiment of the invention, disclosed is a method of removing pieces of tissue from a body of tissue. The method includes rotating a tool having the shank of a tissue removing instrument attached thereto, and moving a tissue engaging portion of the instrument into contact with the tissue to be removed. The tissue is then caused to be wrapped around the tissue engaging portion of the instrument. The tissue is wrapped around the tissue engaging portion of the instrument until the tissue is pulled free from the body of tissue.

In accordance with yet another embodiment of the invention, disclosed is a method of removing granulation tissue from around a tooth. The method includes inserting into a gingival pocket a tissue removing instrument having a tissue engaging member with one or more prongs. A tool to which the tissue removing instrument is attached is caused to be rotated. The rotating tissue engaging member is moved into contact with the granulation tissue so that the prongs grab the granulation tissue, whereupon the granulation tissue is wrapped around the tissue engaging member of the instrument. The granulation tissue is wrapped around the tissue engaging member of the instrument until the granulation tissue is pulled free from around the tooth and from the underlying bone.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts, functions or elements throughout the views, and in which.

DETAILED DESCRIPTION OF THE INVENTION

Figure 1:
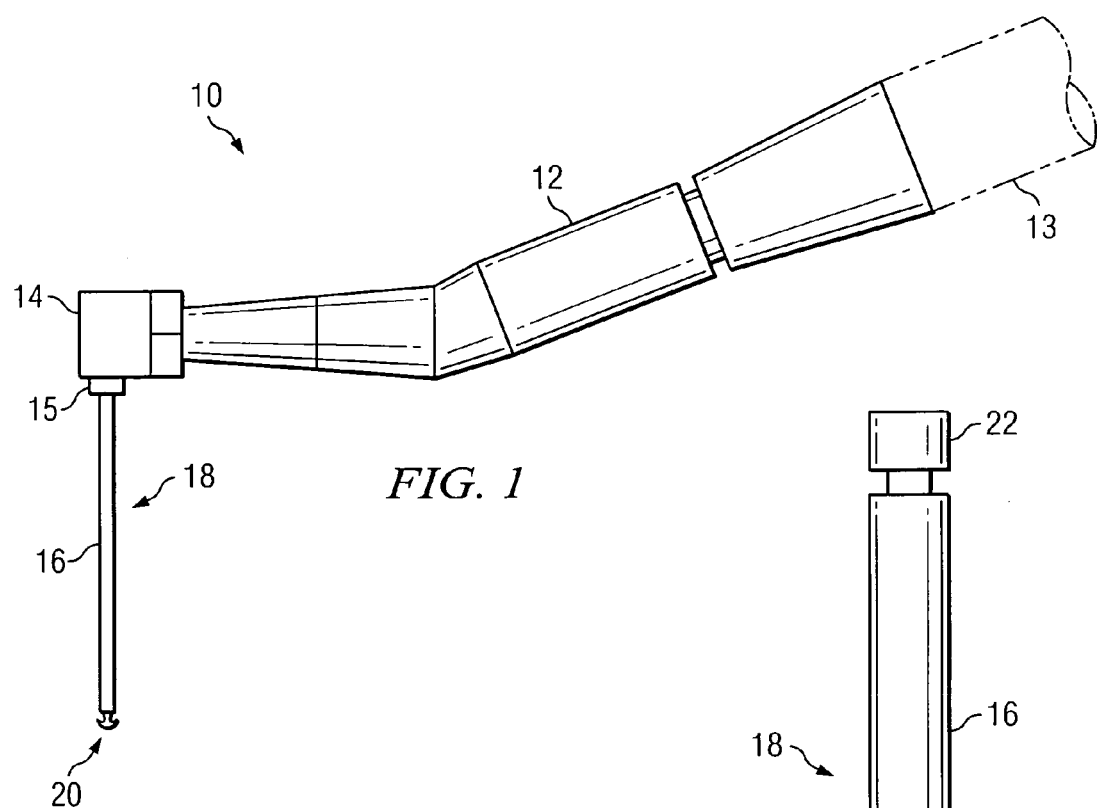
FIG. 1 is a side view illustrating a power-driven tool with which the tissue removing instrument of the invention can be attached.

With reference to FIG. 1, there is shown a power-driven tool with which the tissue removing instrument of the invention is advantageously practiced. The power driven tool 10 is shown as a hand-held device, which may be available in many other forms. The power-driven tool 10 is of conventional construction, including a body 12 which is removably attached to an air-driven rotary motor assembly 13. A head 14 of the tool 10 houses a friction-type chuck 15 for holding the shank 16 of the tissue removing instrument 18 therein. While not shown, the tool 10 includes an internal shaft so that the air-driven motor can rotate the shaft or shank of any instrument or bit inserted into the chuck 15. The instrument 18 includes a tissue engaging member 20 attached to the end of the shank 16. The instrument 18 can be removed from the chuck 15 by forcefully pulling it therefrom.

Figure 2:
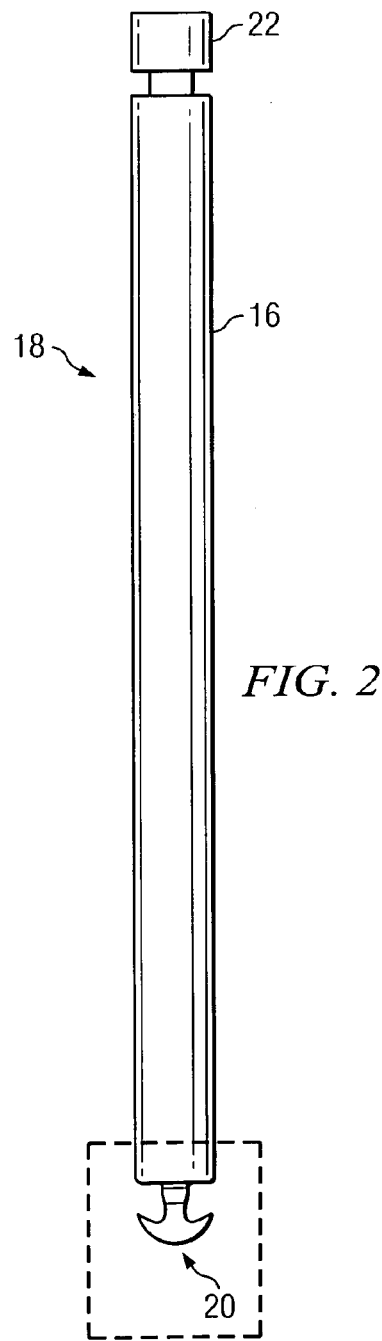
FIG. 2 is an enlargement of the bit constructed according to a preferred embodiment of the invention.
Figure 3:
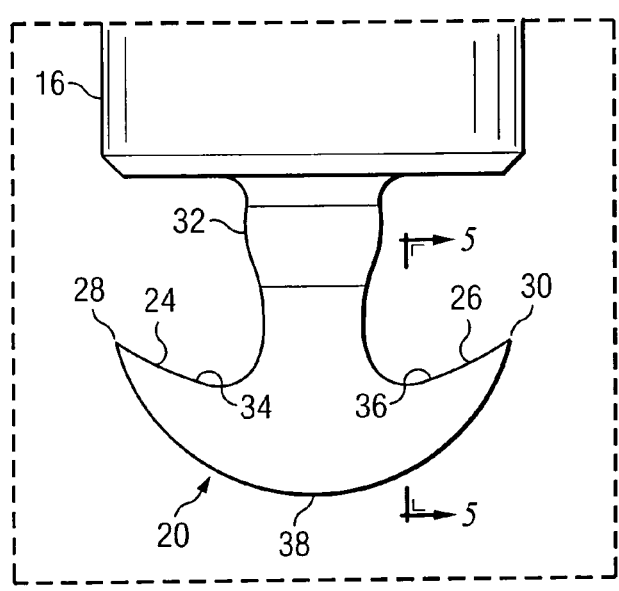
FIG. 3 is an enlargement of a frontal view of the tissue engaging member shown in FIG. 2.
Figure 4:
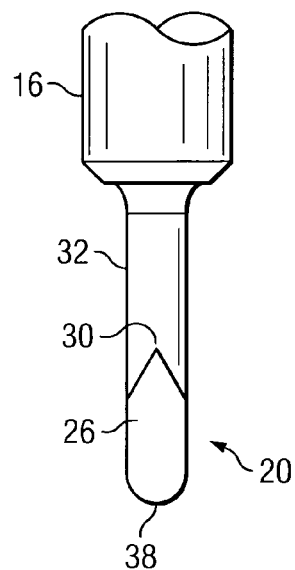
FIG. 4 is a side view of the tissue engaging member shown in FIG. 3.
Figure 5:
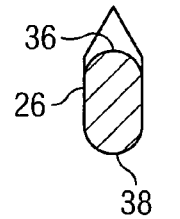
FIG. 5 is a cross-sectional view of a prong of the tissue engaging member, taken along line 5-5 of FIG. 3.

The tissue removing instrument 18 according to one embodiment of the invention is illustrated in FIG. 2, and in the enlargements of FIGS. 3-5. The tissue removing instrument 18 includes a shank 16 with an upper end 22 adapted for use with a dental rotary tool 10 of the type shown in FIG. 1. The tissue engaging member 20 is formed at the opposite end of the shank 16. The shank 16 has a diameter generally larger than the width of the tissue engaging member 20, and includes a smooth and polished outer surface. This construction reduces the instances in which the tissue engaging member 20 will inadvertently contact, erode or damage healthy tissue and bone.

The enlargement of the tissue engaging member 20 of FIG. 3 illustrates the structural features thereof. In the preferred embodiment, the tissue engaging member 20 is crescent shaped with two protrusions. The protrusions comprise wings or prongs 24 and 26. As seen in FIG. 4, the end of each prong 24 and 26 terminates in a respective point 28 and 30. A post 32 joins the tissue engaging member 20 to the end of the shank 16. The other prong 24 is similarly constructed. In a preferred embodiment of the invention, the diameter of the tissue engaging member 20, between the points 28 and 30 of the prongs 24 and 26 is about 0.91 mm. The axial length of the tissue engaging member 20, including the post 32 is about 1.43 mm. The length of the shank 16 is about 35 mm, and the diameter of the shank 16 is between about 1.10 mm and 2.30 mm. The shank 16 can be tapered from a larger diameter at the chuck end, to a smaller diameter at the end to which the tissue engaging member 20 is attached. The width of the tissue engaging member 20, as seen in FIG. 4, is about 0.30 mm. It is to be understood that the size of the tissue engaging member 20 can be other than that noted above.

The tissue removing instrument 18 can be constructed using a rotary abrasive wheel to fabricate and otherwise grind the tissue engaging member 20 in the end of the shank 16. The abrasive wheel can be manipulated around the end of the shank 16 to form the prongs 24 and 26. This procedure can be carried out using a microscope or other magnifying instrument. The mass production of the tissue removing instrument of the invention can be carried out using conventional CNC equipment programmed to form the various shapes and curvatures. It is envisioned that a shank would be held in the chuck of a CNC machine, and a grinding tool moved under computer control to grind the shape of the engaging member therein. The tissue removing instrument 18 can thus be fabricated in the same manner that other miniature surgical and dental tools are made. In the fabrication of the tissue removing instrument, the tissue engaging member can be fabricated separate from the shank, and then laser welded or otherwise fastened to the end of the shank.

Figure 6:
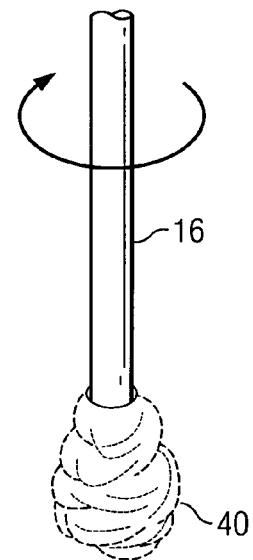
FIG. 6 is a side view of the tissue removing instrument, with a mass of tissue wrapped around it.

The prongs 28 and 30 are especially effective to engage sinewy tissue strands and cause the same to be wrapped around the rotating tissue engaging member 20. When a mass 40 of granulated or other type of tissue is fully wrapped around the tissue engaging member 20, as shown in FIG. 6, the hand tool 10 can be stopped so that the tissue can be manually removed from the instrument 18. The tissue can be removed from the tissue removing instrument 18 by manually pulling it axially off the member 20. Often the tissue is separated into numerous pieces when pulled off the tissue engaging member 20. The bottom arcuate edge 38 of the tissue engaging member 20 is rounded so that if placed into contact with the hard surface of a tooth or bone, the tissue engaging member 20 will not abrade, erode or otherwise remove material from the tooth or bone.

In operation of the tissue removing instrument 18 according to the preferred embodiment, the instrument 18 is secured in a tool to impart rotary movement thereto. Preferably, the tool 10 should be capable of producing rotational speeds between 3,000 and 30,000 rpm, and preferably in the range of about 9,000-11,000 rpm. However, the speed of rotation may not be critical to the operation of the invention. In addition, those skilled in the art may find that different types of tissues can be removed more efficiently using different speed ranges. In any event, the instrument 18 is rotated and moved so that the tissue engaging member 20 is brought into contact with the tissue to be removed. The pointed prongs 24 and 26 quickly engage or grab the tissue and cause it to be quickly wrapped around the rotating member 20. The diseased tissue is eventually dislodge from the damaged bone and from the healthy gingival tissue, and can be extracted from the patient. The removed mass of granulation tissue is then axially pulled off the member 20 from the end, whereupon the instrument 18 is again rotated and re-engaged with the mass of granulation tissue to continue removal of additional portions thereof. When employed to remove granulation tissue from a patient's tooth, it is appreciated that the diseased granulation tissue has a stringy consistency and is weaker than the healthy gingival tissue. The granulation tissue is thus pulled free from the tooth, the damaged bone and the healthy tissue. If necessary, various short strings of granulation tissue that are not separated from the tooth or bone by the tissue removing instrument 18 can be cut by a sharp instrument so that such remnants of tissue can be extracted and removed. The process is continued until all of the granulation tissue is separated from the healthy tissue. In this manner, the removal of the granulation tissue allows the healthy bone and gingival tissue to regenerate so as to repair the gingival pocket and reattach to the tooth.

While the instrument 18 and associated tissue engaging member 20 are effective to remove sinewy-type tissue, such as the granulation tissue encountered in periodontal procedures, the tissue removing instrument 18 can also be advantageously employed in other medical procedures. For example, cartilage can be removed in orthopedic procedures. The rotating member 20 can be engaged with the cartilage tissue and cause it to be wrapped around the bit. The number, size and shape of the protrusions extending radially from the shank of the tissue removing instrument can be adapted to facilitate grabbing the particular type of tissue to be removed.

Figure 7:
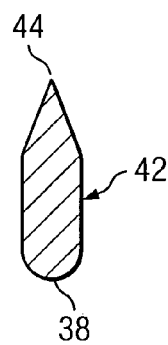
FIG. 7 is a cross-sectional view of a prong having a top knife-like cutting edge to facilitate removal of the tissue from the instrument.

In another embodiment of the invention, the upper edge 34 and 36 of each prong 24 and 26 can be sharpened to respective knife edges to facilitate removal of the tissue wrapped around the instrument 18. This is illustrated in the cross-sectional view of the prong 42 of FIG. 7. The upper edge 44 is sharpened to a knife-like edge to slice the tissue when it is pulled downwardly off the tissue engaging member 20.

The rotating dual pronged tissue engaging member 20 has been found to readily engage the granulation tissue, whereupon the stringy tissue wraps around the member 20 until it is pulled free from its attachment to the bone. The repeated action is effective to clean the periodontal defect surrounding the tooth of the granulation tissue in a short period of time without the use of a curette. However, a curette can be used to remove minute remnants of the granulation tissue from the tooth after the major portion has been removed by the tissue removing instrument 18 of the invention. The overall procedure in much easier, less tedious, and requires less time. It has been found that when using the tissue engaging member 20 of the FIG. 3 embodiment, the granulation tissue can be removed from a tooth in as few as one minute, or less.

Figure 8:
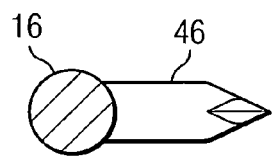
FIG. 8 is an illustration of a single prong tissue engaging member constructed according to another embodiment of the invention.

While two prongs of the tissue engaging member are effective to grab the tissue and cause it to be wrapped around the member 20, it is believed that other numbers of prongs would be effective also, including a single prong as shown in FIG. 8. Here, a single rotating prong 46 can grab the tissue and as the instrument rotates, whereupon the tissue wraps around the member and is removed from the tooth. The single prong 46 is constructed in the same manner as the prong 26 of FIG. 3.

Figure 9:
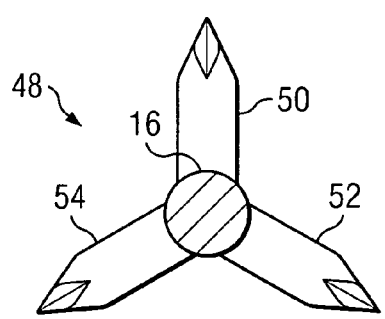
FIG. 9 is an illustration of a three-prong tissue engaging member constructed according to another embodiment of the invention.
Figure 10:
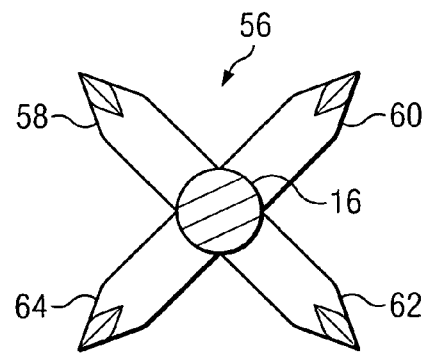
FIG. 10 is an illustration of a four-prong tissue engaging member constructed according to another embodiment of the invention.

The tissue engaging member 48 of FIG. 9 is constructed with three prongs 50, 52 and 54 spaced around the shank 16 of the instrument. Again, the prongs 50-54 can be constructed in the same manner as the prongs 24 and 26 of FIG. 3. FIG. 10 is another embodiment of a tissue engaging member 56 with four prongs 58-64, where each prong is constructed in the same manner as the prong 26 of FIG. 3. Tissue engaging members having more than four prongs arranged around the shank 16 could be effective, but as the number of prongs formed around the shank at the same longitudinal location increases, it is believed that the effectiveness in grabbing the tissue decreases. In other words, if twenty or more prongs were formed around the shank 16 at the same longitudinal location, the effectiveness in grabbing the tissue would be decreased, as compared to a few prongs. In addition, as the number of prongs increase, the complexity in fabricating the instrument increase, as does the cost.

Figure 11:
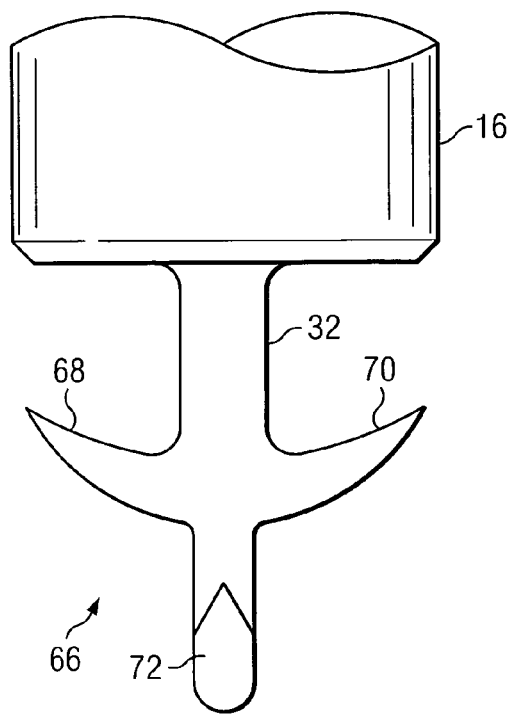
FIG. 11 is an illustration of another arrangement of a four-prong tissue engaging member constructed according to another embodiment of the invention.

The tissue engaging member 66 of FIG. 11 is constructed with four prongs, but not all of the prongs are formed at the same longitudinal location on the shank 16. Two opposed prongs 68 and 70 are located at one longitudinal location on the shank 16, and two other prongs, one shown as prong 72, are formed at a different longitudinal location on the shank 16. The two prongs 68 and 70 are formed above the prongs 72. Moreover, the upper prongs 68 and 70 are fabricated at the 0° and 180° locations on the shank 16, and the lower prongs 72 are fabricated at the 90° and 270° locations.

Figure 12:
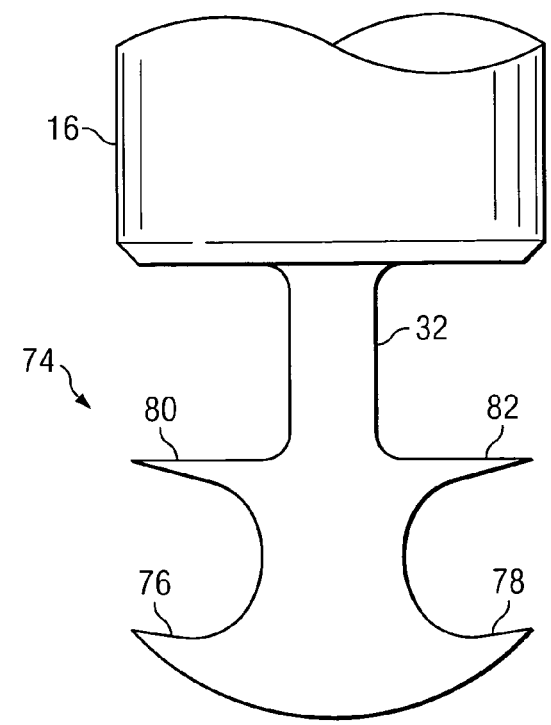
FIG. 12 is an illustration of a multi-tiered, multiple-prong tissue engaging member constructed according to another embodiment of the invention.

A tissue engaging member 74 of a different configuration is shown in FIG. 12. The member 74 has a lower set of prongs 76 and 78, and an upper set of prongs 80 and 82. The upper prongs 80 and 82 are located on the shank 16 above the respective lower prongs 76 and 78. The tissue engaging member 74 could be constructed with another pair of upper prongs and another pair of lower prongs, where each upper prong would be 90° apart, and each lower prong would also be 90° apart. Again, the upper prongs could be shifted around the shank 16 so as not to be axially aligned with the corresponding lower prongs.

Figure 13:
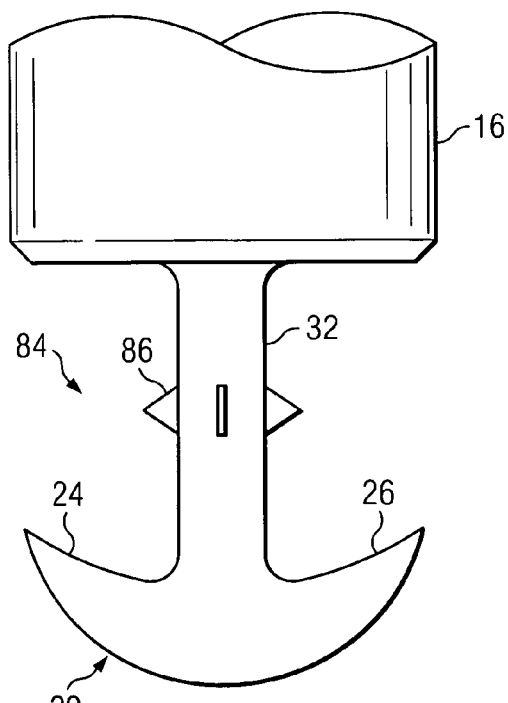
FIG. 13 an illustration of a two-prong tissue engaging member equipped with plural barbs.

FIG. 13 illustrates yet another embodiment of a tissue engaging member 84 constructed according to the invention. The two lower prongs 24 and 26 are constructed in the same manner as noted above in connection with the member 20 of FIG. 3. In addition to the prongs 24 and 26, the member 84 is constructed with one or more additional protrusions in the nature of barbs 86. The barbs 86 are pointed and are effective to grab the tissue strands and anchor the tissue so that the rotating instrument wraps the strands of tissue around the tissue engaging member 84. While four barbs 86 are illustrated, any number of barbs can be utilized. The barbs 86 can be located at any location adjacent the prongs 24 and 26. Indeed, those skilled in the art may find that the barbs 86 can even be located on the prongs. There may be more than one longitudinal location at which the barbs are formed. While the barbs are shown as triangular-shaped members, other shapes can be employed with equal effectiveness. As yet another alternative, the tissue engaging member can be constructed using only barbs, and without prongs.

Figure 14:
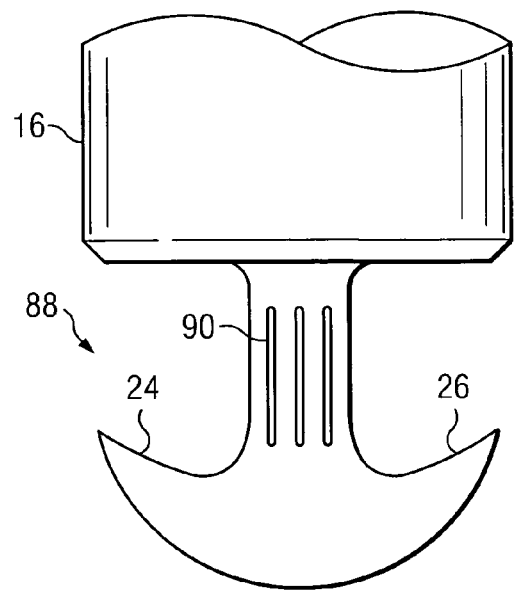
FIG. 14 is an illustration of a tissue engaging member having a post connecting the prongs to the end of the shank, where the post is roughened with plural grooves.

As an alternative, or in addition to the barbs 86, the post 32 of the tissue engaging member 88 of FIG. 14 can be fabricated with a roughened surface, such as longitudinal grooves to facilitate grabbing the tissue strands. The longitudinal grooves are shown as numeral 90. The longitudinal grooves 90 can be formed on the post 32 using a laser or other etching technique. In order to increase the tissue grabbing ability of the tissue engaging member, the entire surface or portions thereof could be roughened by laser or chemical etching techniques.

The various embodiments of the tissue engaging member described above can be formed on the end of the shank 16 by various techniques, including those described above. In order to overcome the need to sterilize the instrument after each use, it is envisioned that the tissue removing instrument would be disposable. However, the tissue removing instrument is constructed of stainless steel or other suitable surgical steel and could be sterilized using conventional equipment, such as an autoclave.

While the preferred and other embodiments of the invention have been disclosed with reference to specific tissue engaging members, and associated methods of use thereof, it is to be understood that many changes in detail may be made as a matter of engineering choices without departing from the spirit and scope of the invention, as defined by the appended claims.

What is claimed is:

1. A method of removing pieces of tissue from a body of tissue, comprising the steps of:

rotating a tissue removing instrument having a shank attached thereto;

inserting a tissue engaging portion of the tissue removing instrument into a gingival pocket to remove granulation tissue around a tooth;

causing the granulation tissue to be wrapped around the tissue engaging portion of the tissue removing instrument; and wrapping the granulation tissue around the tissue engaging portion of the tissue removing instrument until the granulation tissue is pulled free from the tooth.

2. The method of claim 1, further including rotating the tissue removing instrument with an rpm greater than about 1,000.

3. The method of claim 1, further including rotating the tissue removing instrument with an rpm greater than about 9,000.

4. The method of claim 1, further including removing the granulation tissue wound around the tissue engaging portion of the tissue removing instrument by pulling the granulation tissue axially off the instrument.

5. The method of claim 1, further including removing the granulation tissue from the tooth without cutting the granulation tissue with a sharp edge of the tissue engaging portion of the tissue removing instrument.

6. A method of removing granulation tissue from bone to which a tooth is anchored, comprising the steps of:
   inserting into a gingival pocket a tissue removing instrument having a tissue engaging member with one or more prongs;
   rotating a tool to which the tissue removing instrument is attached;
   moving the rotating tissue engaging member into contact with the granulation tissue so that the one or more prongs grab the granulation tissue;
   causing the granulation tissue to be wrapped around the tissue engaging member of the instrument; and
   wrapping the granulation tissue around the tissue engaging member of the instrument until the granulation tissue is pulled free from the bone and the tooth.

7. The method of claim 6, further including wrapping a mass of granulation tissue around the tissue engaging member.

8. The method of claim 7, further including removing the mass of granulation tissue from the tissue engaging member, and again engaging the tissue engaging member with the granulation tissue to remove subsequent portions from the bone until substantially all of the granulation tissue has been removed.

9. The method of claim 7, further including pulling the mass of granulation tissue wrapped around the tissue engaging member axially off the instrument, and slicing the mass of granulation tissue with a sharp edge of the tissue engaging member to facilitate removal of the mass of granulation tissue from the instrument.

10. The method of claim 6, further including disposing of the tissue removing instrument after a single use thereof in removing substantially all of the granulation tissue from a patient.

\* \* \* \* \*